United States Patent [19]
Kwon

[11] Patent Number: 5,836,299
[45] Date of Patent: Nov. 17, 1998

[54] SEALS FOR USE IN AN AEROSOL DELIVERY DEVICE

[75] Inventor: Oh-Seung Kwon, Woodbury, Minn.

[73] Assignee: Minnesota Mining & Manufacturing Co., St. Paul, Minn.

[21] Appl. No.: 397,546

[22] Filed: Feb. 28, 1995

Related U.S. Application Data

[63] Continuation of Ser. No. 92,001, Jul. 15, 1993, abandoned.

[51] Int. Cl.$^6$ .................................................. B65D 83/14
[52] U.S. Cl. ............................ 128/200.23; 128/200.14; 222/402.1; 222/394; 222/372; 424/45
[58] Field of Search ................................ 424/43, 45, 47; 222/373, 402, 398, 394, 402.1, 395, 399, 372; 239/338; 252/305; 128/200.23, 200.14

[56] References Cited

U.S. PATENT DOCUMENTS

| | | | |
|---|---|---|---|
| 2,721,010 | 10/1955 | Meshberg | 222/394 |
| 2,886,217 | 5/1959 | Thiel | 222/394 |
| 2,892,576 | 6/1959 | Ward | 222/394 |
| 2,968,427 | 1/1961 | Meshberg | 222/394 |
| 2,980,301 | 4/1961 | De Gorter | 222/394 |
| 3,049,269 | 8/1962 | Gawthrop | 222/307 |
| 3,052,382 | 9/1962 | Gawthrop | 222/335 |
| 4,340,684 | 7/1982 | Bohm et al. | 525/194 |
| 4,407,481 | 10/1983 | Bolton et al. | 251/353 |
| 4,819,834 | 4/1989 | Thiel | 222/355 |
| 5,112,660 | 5/1992 | Saito et al. | 428/36.8 |
| 5,225,183 | 7/1993 | Purewal et al. | 424/45 |
| 5,474,758 | 12/1995 | Kwon | 424/45 |

FOREIGN PATENT DOCUMENTS

| | | |
|---|---|---|
| 2549568 | 1/1985 | France . |
| 269081 | 11/1991 | Japan . |
| 2077229 | 12/1981 | United Kingdom . |
| US91/09726 | 7/1992 | WIPO . |
| 93/22221 | 11/1993 | WIPO . |

OTHER PUBLICATIONS

Petition and Particulars of Objection (with exhibits) filed in the matter of European Patent (UK) No. 0,708,805 by Bespak plc, United Kingdom Patents Court, High Court of Justice, Chancey Division, CH–1998–B–No. 4600 (Aug. 19, 1998).

Encyclopedia of Polymer Science & Engineering, vol. 6, 522–548, John Wiley & Sons (1985).

*Journal of Japan Rubber Society,* 64, 161 Hiramatsu et al. (1991).

"Thermoplastic Elastomers", paper number 27, American Chemical Society Rubber Division, Rader (1992).

"Elastomeric Alloys", paper No. 30, American Chemical Society Rubber Division, Puydak, (1992).

"Thermoplastic Elastomers Prepared by Dynamic Vulcanization", paper No. 41, American Chemical Society Rubber Division, Coran et al. (1992).

"TPEs in Household Appliances Using and Delivering Water", paper No. 69, American Chemical Society Rubber Division, Mattix et al., (1992).

*Rubber Chem. Technol.* 53, 141 Coran et al., (1980).

*Primary Examiner*—Raj Bawa
*Attorney, Agent, or Firm*—Mary Susan Howard; Ted K. Ringsred

[57] ABSTRACT

A device for delivering an aerosol, comprising: a casing member, a valve stem, and a diaphragm. The diaphragm is made of an ethylene-propylene-diene rubber ("EPDM") and is stable to dimensional change when exposed to 1,1,1,2-tetrafluoroethane or 1,1,1,2,3,3,3-heptafluoroethane.

8 Claims, 1 Drawing Sheet

SEALS FOR USE IN AN AEROSOL DELIVERY DEVICE

This is a continuation of application Ser. No. 08/092,001, filed Jul. 15, 1993, now abandoned.

TECHNICAL FIELD

This invention relates to devices for delivering aerosols. In another aspect this invention relates to sealing members. In yet another aspect this invention relates to sealing members for use in devices for delivering aerosols.

DESCRIPTION OF THE RELATED ART

The continuing use of aerosol formulations comprising conventional chlorofluorocarbon propellants is being debated due to the suspected role of such propellants in atmospheric depletion of ozone. Accordingly, formulations based on alternative propellants such as HFC-134a (1,1,1, 2-tetrafluoroethane) and HFC-227 (1,1,1,2,3,3,3-heptafluoropropane) are being developed to replace those conventional propellants thought to contribute to atmospheric ozone depletion.

Containers for aerosol formulations commonly comprise a vial body coupled to a valve ferrule. The valve ferrule comprises a valve stem through which the formulation is dispensed. Generally the valve ferrule includes a rubber valve seal (a diaphragm) intended to allow reciprocal movement of the valve stem while preventing leakage of propellant from the container. These rubber valve seals are commonly made of thermoset rubbers such as butyl rubber, butadiene-acrylonitrile ("Buna") rubbers, and neoprene (polychloroisoprene), which are compounded with vulcanizing agents prior to being fashioned into valve seals.

It has been found that some conventional devices for delivering aerosols suffer impaired performance when used in connection with HFC-134a or HFC-227. Selection of suitable materials for use as diaphragms to contain aerosol formulations based on these alternative propellants is complicated by interactions between the seal material and the formulation components, including the propellant. Conventional devices involving diaphragms of neoprene (polychloroprene), butyl rubber, or butadieneacrylonitrile "buna" rubbers allow substantial leakage of HFC-134a or HFC-227 from some formulations over time. Particularly in low volume formulations such as pharmaceutical formulations for use in inhalation therapy, this leakage can cause a substantial increase in concentration of the active ingredient in the formulation, resulting in delivery of an improper dose. Furthermore, with some formulations the valve stem tends to stick, pause, or drag during the actuation cycle.

Certain thermoplastic elastomers have found use as improved seal materials in aerosol canisters.

For example, valve seals comprising certain styrene-ethylene/butylene-styrene block copolymers are disclosed in commonly assigned copending application Ser. No. 07/878, 041. Also, valve seals comprising certain copolymers of ethylene and either butene, hexene, or octene are disclosed in PCT US91/09726 (Marecki).

Vulcanized ethylene-propylene-diene (EPDM) rubbers have been used as materials of construction in hoses for transporting refrigerant fluids including HFC-134a (see, e.g., U.S. Pat. No. 5,112,660, Saito et al.). EPDM rubber treated with a silicone adhesive agent has also been proposed for use in combination with a polytetrafluoroethylene lip as a component of a seal for a rotating shaft of a compressor for use with mixtures of HFC-134a and a polyalkylene glycol refrigerator oil. *Journal of Japan Rubber Society*, 1991, 64, 161 (Hiramatsu et al.). EPDM rubbers have not been used in applications involving a reciprocating dynamic seal (that is, a seal between components that reciprocate relative to and in contact with the seal) for containing HFC-134a. EPDM rubbers have been incorporated into materials known as thermoplastic elastomer blends and thermoplastic elastomer alloys. These materials involve a dispersion of an elastomeric EPDM in a thermoplastic matrix (e.g., polyethylene or polypropylene). Such materials have been used as gasket materials, e.g., in automotive applications. There is nothing to suggest, however, that such materials would be suitable for use in fashioning a diaphragm for use in containing an aerosol formulation based on HFC-134a or HFC-227.

SUMMARY OF THE INVENTION

This invention provides a device for delivering an aerosol, comprising: a valve stem, a diaphragm having walls defining a diaphragm aperture, and a casing member having walls defining a casing aperture, wherein the valve stem passes through the diaphragm aperture and the casing aperture and is in slidable sealing engagement with the diaphragm aperture, and wherein the diaphragm is in sealing engagement with the casing member, the diaphragm being stable to dimensional change when exposed to 1,1,1,2-tetrafluoroethane and comprising an ethylene-propylene-diene rubber, further characterized in that the diaphragm material exhibits a leak rate of less than about 500 mg/year when tested according to the Leak Rate Test Method.

This invention also provides a metered-dose device for delivering an aerosol that comprises, in addition to the above-discussed valve stem, diaphragm, and casing member, a tank seal having walls defining a tank seal aperture, and a metering tank of a predetermined volume and having an inlet end, an inlet aperture, and an outlet end, wherein the outlet end is in sealing engagement with the diaphragm, the valve stem passes through the inlet aperture and the tank seal aperture and is in slidable engagement with the tank seal aperture, and the tank seal is in sealing engagement with the inlet end of the metering tank, and wherein the valve stem is movable between an extended closed position, in which the inlet end of the metering tank is open and the outlet end is closed, and a compressed open position in which the inlet end of the metering tank is substantially sealed and the outlet end is open.

In a preferred embodiment the casing member defines a formulation chamber, and in a further preferred embodiment the formulation chamber contains an aerosol formulation comprising a propellant, said propellant comprising 1,1,1, 2-tetrafluoroethane or 1,1,1,2,3,3,3-heptafluoropropane.

This invention also provides a device for delivering an aerosol, comprising: a valve stem, a diaphragm comprising an ethylene-propylene-diene rubber and having walls defining a diaphragm aperture, and a casing member having walls defining a formulation chamber and a casing aperture, wherein the valve stem passes through the diaphragm aperture and the casing aperture and is in slidable sealing engagement with the diaphragm aperture, and wherein the diaphragm is in sealing engagement with the casing member, the device having contained in the formulation chamber thereof a medicinal aerosol formulation, and wherein the diaphragm is stable to dimensional change when exposed to the medicinal aerosol formulation.

Devices of this invention find particular use in connection with aerosol formulations involving HFC-134a or HFC-227 as a propellant. Leakage and smoothness of operation are improved in the devices of the invention compared to like devices involving the conventional diaphragm materials.

BRIEF DESCRIPTION OF THE DRAWINGS

The drawing is represented by FIGS. 1 and 2.

DETAILED DESCRIPTION OF THE INVENTION

Figures 1, 2:
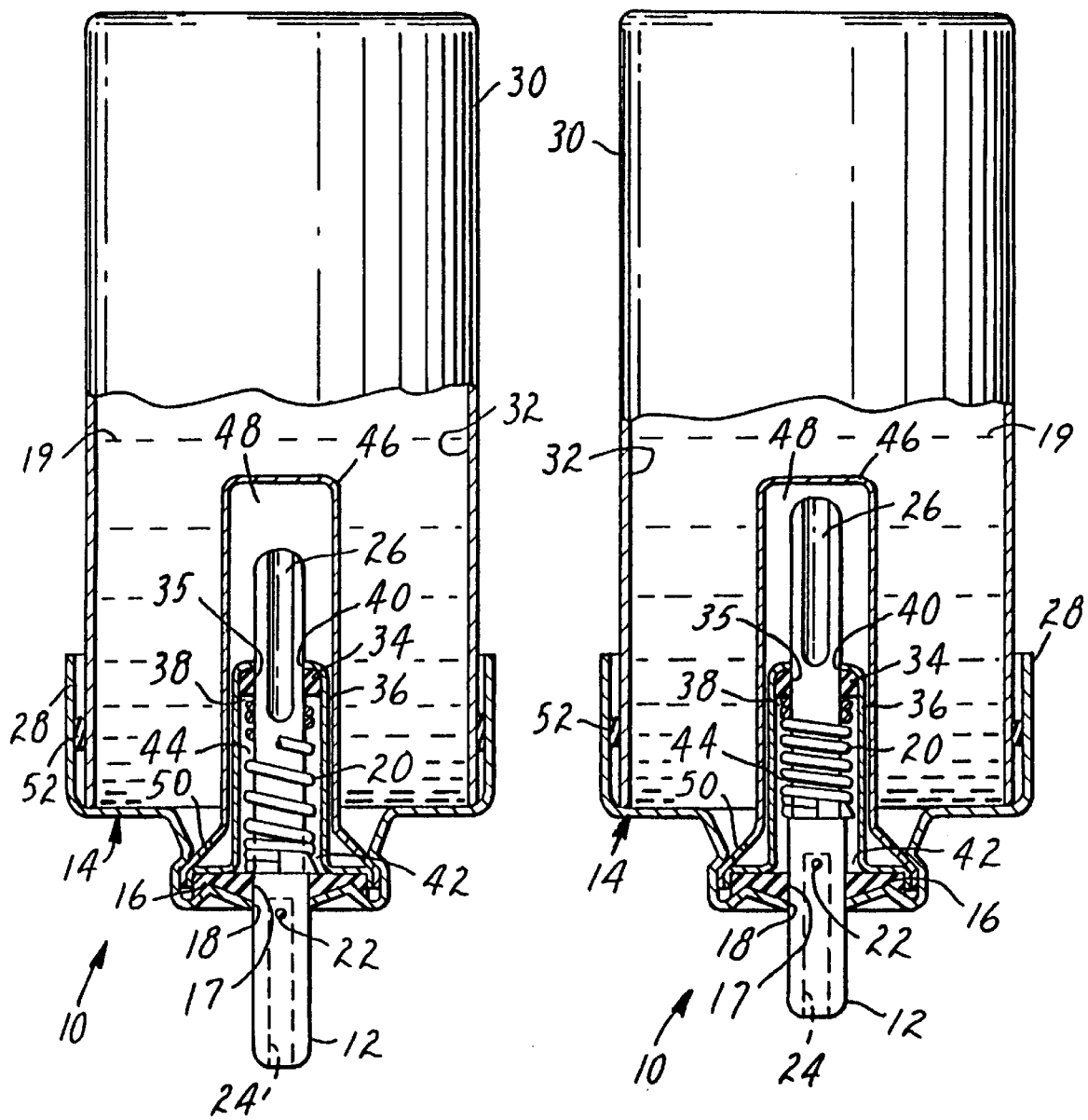
FIG. 1 is a partial cross-sectional view of one embodiment of a device of the invention, wherein the valve stem is in the extended closed position.
FIG. 2 is a partial cross-sectional view of the embodiment illustrated in FIG. 1, wherein the valve stem is in the compressed open position.

As used herein the term "stable to dimensional change when exposed to 1,1,1,2-tetrafluoroethane" means that a diaphragm having a thickness of about 1.0 mm (0.040 inch), an inside diameter of about 2.5 mm (0.10 inch), and an outside diameter of about 8.6 mm (0.34 inch) will maintain its original inside and outside diameter within eight percent (or less if a lesser percentage is stated) when soaked (i.e., submerged) in 1,1,1,2-tetrafluoroethane for 30 days at 20° C. and analyzed according to the Swelling Test Method set forth below. Likewise a material stable to dimensional change when exposed to any other substance (e.g., HFC-227 or an aerosol formulation) is defined in the same manner but using the particular substance as the soaking liquid.

In order to minimize and/or prevent leakage of refrigerants, propellants, or other formulation components, especially propellants such as 1,1,1,2-tetrafluoroethane and 1,1,1,2,3,3,3-heptafluoropropane, from a sealed chamber, this invention provides a device comprising an elastomeric sealing member. The sealing member is in the form of a diaphragm for use in connection with an aerosol formulation, preferably a pharmaceutical aerosol formulation, and exhibits a leak rate of less than about 500 mg/year, more preferably less than about 300 mg/year when tested according to the Leak Rate Test Method set forth below.

A sealing member for use in a device of the invention comprises an elastomer comprising an ethylene-propylene-diene rubber ("EPDM"). Such rubbers are well known and disclosed, e.g., in Encyclopedia of Polymer Science & Engineering, Vol. 6, pp. 522–548, John Wiley & Sons, 1985, and in *Developments in Rubber Technology and Synthetic Rubbers*, Vol. 2, Applied Science Publishers, New York, 1981, Chapter 4, p. 87. Generally the diene component of an EPDM base rubber can be any suitable non-conjugated diene, e.g., a linear diene such as 1,4-hexadiene, or a bicyclic diene such as dicyclopentadiene, methylenenorbornene, methyltetrahydroindene, or the like. The EPDM base rubber can be crosslinked by vulcanization to various degrees in order to obtain desirable hardness and compression set properties (discussed below). The EPDM can also contain conventional polymer additives such as processing aids, colorants, tackifiers, lubricants, silica, talc, or processing oils such as mineral oil in suitable amounts readily selected by those skilled in the art. The EPDM is preferably free of adhesive agents such as silicone adhesive agents.

The sealing member can contain an EPDM (with or without such optional polymer additives) as substantially the only polymer component. In another embodiment the EPDM is present as part of a thermoplastic elastomer blend or alloy, that is, it is present, e.g., in the form of particles, substantially uniformly dispersed in a continuous thermoplastic matrix. Particle size of the EPDM can be readily selected by those skilled in the art. Suitable thermoplastic matrices are selected in order to provide a blend or alloy that has appropriate processing characteristics (e.g., melting point). Exemplary matrix materials include polyethylene and preferably polypropylene. The degree of crosslinking (vulcanization) of the EPDM, the particle size of the EPDM, and the relative amounts of the EPDM and the thermoplastic matrix material are selected in order to provide suitable hardness and compression set.

Excessive permeability of the diaphragm to an aerosol propellant will render an aerosol device unsuitable for containing the propellant. The diaphragm material in a device of the invention, however, has a suitably low permeability to 1,1,1,2-tetrafluoroethane or 1,1,1,2,3,3,3-heptafluoropropane in order that the leak rate of a device of the invention is suitable for pharmaceutical applications (e.g., less than about 500 mg/year when tested according to the Leak Rate Test Method described below). Materials of suitably low permeability can be selected readily by those skilled in the art. For example, permeability of EPDM materials to 1,1,1,2-tetrafluoroethane is known to vary with the iodine value of the EPDM and with the amount of process oil incorporated in the EPDM (see, e.g., U.S. Pat. No. 5,112,660, Saito et al., incorporated herein by reference).

It has been found that excessive expansion or contraction of the diaphragm in an aerosol valve can result in an ineffective dynamic seal between the valve stem and the diaphragm. EPDM materials, however, have been found to be dimensionally stable when exposed to 1,1,1,2-tetrafluoroethane or 1,1,1,2,3,3,3-heptafluoropropane. It is preferred that the diaphragm material be stable to dimensional change (as that term is defined above) such that diaphragm dimensions change no more than about 8%, preferably no more than about 5%, and most preferably no more than about 3%.

Shore A hardness of a diaphragm material for use in the invention is preferably between about 50 and about 90, more preferably between about 70 and about 85. Also, it is preferred that the material have a suitable compression set in order that the static seal between the diaphragm and the other components of the device (e.g., the valve ferrule and the metering tank of the device illustrated in the accompanying Drawing) remains adequate over the life of the device. Compression set can be measured by ASTM D 395 (incorporated by reference). Values of less than about 40, more preferably less than about 35, and most preferably less than about 20 are desirable (measured at 70 hours, 20° C. according to Method B of ASTM D 395).

Certain suitable elastomers are commercially available. Among EPDM rubbers is included KL70L3841 or KL3866 (Kirkhill Rubber Company, Brea, Calif.). Other suitable EPDMs can be prepared using methods known to those skilled in the art and described generally in Encyclopedia of Polymer Science & Engineering, Vol. 6, pp. 522–548, John Wiley & Sons, 1985. Among the thermoplastic elastomer blends and alloys are included SANTOPRENE™ elastomers 271-64, 271-73, and 271-80 (Advanced Elastomer Systems, Akron, Ohio). Other suitable blends and alloys can be prepared using methods known to those skilled in the art and disclosed, e.g., in "Thermoplastic Elastomers Prepared by Dynamic Vulcanization", paper number 41, American Chemical Society Rubber Division, November 1992 (Coran et al.) and *Rubber Chem. Technol.* 1980, 83, 141 (Coran et al.), both of which are incorporated herein by reference. Preferred elastomers include those commercial materials enumerated above.

The device of the invention will be described with reference to the Drawing. FIG. 1 shows device 10 comprising valve stem 12, casing member 14, and diaphragm 16. The casing member has walls defining casing aperture 18, and the diaphragm has walls defining diaphragm aperture 17. The valve stem passes through and is in slidable sealing engagement with the diaphragm aperture. The diaphragm is also in sealing engagement with casing member 14. Diaphragm 16 represents an elastomeric sealing member. Such a sealing member can be one piece or it can be in the form of a plurality of thinner layers arranged in a stack.

The illustrated embodiment is a device for use with pharmaceutical formulations. The diaphragm in the illustrated embodiment is a single piece of a thickness sufficient to form an effective seal with the casing member, preferably about 0.125 mm (0.005 inch) to about 1.25 mm (0.050 inch). It has an outside diameter of about 8.6 mm (0.340 inch), and an inside diameter sufficient to form an effective seal with the valve stem. As valve stems having an outside diameter of about 2.79 mm (0.110 inch) are commonly used, suitable diaphragm inside diameter can be in the range of about 2.03 mm (0.080 inch) to about 2.67 mm (0.105 inch). Diaphragm dimensions suitable for use with other general types of devices can be easily selected by those skilled in the art.

Valve stem 12 is in slidable engagement with diaphragm aperture 17. Helical spring 20 holds the valve stem in an extended closed position as illustrated in FIG. 1. Valve stem 12 has walls defining orifice 22 which communicates with exit chamber 24 in the valve stem. The valve stem also has walls defining channel 26.

In the illustrated embodiment casing member 14 comprises mounting cup 28 and canister body 30 and defines formulation chamber 32. The illustrated embodiment further comprises tank seal 34 having walls defining tank seal aperture 35, and metering tank 36 having inlet end 38, inlet aperture 40, and outlet end 42. The metering tank also has walls defining metering chamber 44 of predetermined volume (e.g., 50 $\mu$L). Outlet end 42 of metering tank 36 is in sealing engagement with diaphragm 16, and valve stem 12 passes through inlet aperture 40 and is in slidable engagement with tank seal 34.

When device 10 is intended for use with a suspension aerosol formulation it further comprises retaining cup 46 fixed to mounting cup 28 and having walls defining retention chamber 48 and aperture 50. When intended for use with a solution aerosol formulation retaining cup 46 is optional. Also illustrated in device 10 is sealing member 52 in the form of an O-ring that substantially seals formulation chamber 32 defined by mounting cup 28 and canister body 30. Sealing member 52 preferably comprises the elastomer described above.

Operation of device 10 is illustrated in FIGS. 1 and 2. In FIG. 1, the device is in the extended closed position. Aperture 50 allows open communication between retention chamber 48 and formulation chamber 32, thus allowing the aerosol formulation to enter the retention chamber. Channel 26 allows open communication between the retention chamber and metering chamber 44 thus allowing a predetermined amount of aerosol formulation to enter the metering chamber through inlet aperture 40. Diaphragm 16 seals outlet end 42 of the metering tank.

FIG. 2 shows device 10 in the compressed open position. As valve stem 12 is depressed channel 26 is moved relative to tank seal 34 such that inlet aperture 40 and tank seal aperture 35 are substantially sealed, thus isolating a metered dose of formulation within metering chamber 44. Further depression of the valve stem causes orifice 22 to pass through aperture 18 and into the metering chamber, whereupon the metered dose is exposed to ambient pressure. Rapid vaporization of the propellant causes the metered dose to be forced through the orifice, and into and through exit chamber 24. Device 10 is commonly used in combination with an actuator that facilitates inhalation of the resulting aerosol by a patient.

A particularly preferred device of the invention is a metered dose configuration substantially as described above and illustrated in the Drawing. Other particular configurations, metered dose or otherwise, are well known to those skilled in the art and suitable. For example the devices described in U.S. Pat. Nos. 4,819,834 (Thiel), 4,407,481 (Bolton), 3,052,382 (Gawthrop), 3,049,269 (Gawthrop), 2,980,301 (DeGorter), 2,968,427 (Meshberg), 2,892,576 (Ward), 2,886,217 (Thiel), and 2,721,010 (Meshberg) (all incorporated herein by reference) involve a valve stem, a diaphragm, and a casing member in the general relationship described herein. Generally any and all sealing members (such as diaphragms, seals, and gaskets) that serve to minimize and/or prevent escape of components, especially propellant, from such assemblies can comprise the above described elastomer.

The devices of the invention find particular use with aerosol formulations involving a propellant comprising HFC-134a or HFC-227. Any such formulation can be used. Pharmaceutical formulations are preferred.

Preferred pharmaceutical formulations generally comprise HFC-134a or HFC-227 in an amount effective to function as an aerosol propellant, a drug having local or systemic action and suitable for use by inhalation, and any optional formulation excipients. Exemplary drugs having local effect in the lung include bronchodilators such as albuterol, formoterol, pirbuterol, and salmeterol, and pharmaceutically acceptable salts and derivatives thereof, and steroids such as beclomethasone, fluticasone, and flunisolide, and pharmaceutically acceptable salts, derivatives, solvates, and clathrates thereof. Exemplary drugs having systemic effect include peptides such as insulin, calcitonin, interferons, colony stimulating factors, and growth factors. The drug is present in the formulation in an amount sufficient to provide a predetermined number of therapeutically effective doses by inhalation, which can be easily determined by those skilled in the art considering the particular drug in the formulation. Optional excipients include those disclosed, e.g., in EP-A-372,777 (Purewal et al., incorporated herein by reference), and others known to those skilled in the art.

Depending upon the particular configuration of a device of the invention, a pharmaceutical aerosol formulation can be filled into an aerosol canister of the invention, e.g., by conventional pressure filling or cold filling methods. The formulation can then be administered by inhalation (e.g., to the lung) by coupling the aerosol canister to an aerosol actuator and dispensing the formulation via the actuator.

Diaphragm Preparation

Diaphragms can be prepared by conventional techniques known to those skilled in the art, such as compression molding, extrusion, and injection molding. The EPDM rubber diaphragms exemplified herein were die cut from a sheet prepared by the vendor. The thermoplastic elastomer blend diaphragms exemplified herein were prepared according to the general method set forth below:

Extrusion

A sample of a selected elastomer is fed into the feed throat of a Haake RHEOCOR™ single-screw extruder fitted with a Haake RHEOMIX™ three-zone extruder head and equipped with a 1.9 cm (0.75 inch) diameter screw having a 3:1 pitch and a length to diameter ratio of 25:1 (screw speed: 180 rpm; extruder temperature: 171° C. zone 1, 182° C. zone 2, 199° C. zone 3; die temperature: 210° C.; melt temperature: 164° C). The melt is extruded through a flat film die, fitted with a shim to provide the desire opening, and over a cooled chrome roller. The thickness of the resulting sheet is controlled by appropriate adjustment of screw speed and speed of the cooled roller. Diaphragms are hand cut from the sheet with a die of appropriate size.

Test Methods

Sealing members were tested as follows:

Leak Rate

Aerosol canister bodies (10 mL) are filled with an aerosol formulation and fitted with a metered dose valve substantially as described and illustrated above and comprising a diaphragm of a selected size and material. The valve is actuated several times in order to assure its function. The mass of the filled device is measured. The filled device is allowed to stand under the indicated conditions for a period of time, after which time mass is again measured. The loss of mass over time is extrapolated to one year and reported in mg/year.

As used in the claims below the "Leak Rate Test Method" involves twenty-five independent determinations as described above, using HFC-134a as the aerosol formulation and using a valve having a stainless steel valve stem with a 2.79 mm (0.110 inch) outside diameter and fitted with a diaphragm of the specified diaphragm material. The diaphragm is 0.89 mm (0.035 inch) thick having an inside diameter of 2.41 mm (0.095 inch), and having an outside diameter of 8.64 mm (0.34 inch).

Valve Delivery

The mass of a filled device is measured. The device is then inverted and actuated one time. Mass is again determined and the valve delivery is recorded as the difference. Measurement of through life valve delivery involves making the above-described valve delivery measurement for each actuation of a valve until the formulation is expired (typically about 200 actuations).

Swelling

Diaphragms having a thickness of about 1.0 mm (0.040 inch), an inside diameter of about 2.5 mm (0.10 inch) and an outside diameter of about 8.6 mm (0.34 inch) are placed in a transparent closed measuring chamber (Comes Maschinenbou AG, Möhlin, Switzerland). The cell is filled with a soaking liquid and stored at the indicated temperature for the indicated period of time. The dimensions of the diaphragms are measured by viewing the diaphragms with a microscope through the window of the cell. Change of inside diameter and outside diameter is recorded as the average of three independent determinations.

The formulations used in the TABLES below in order to demonstrate the invention are as follows, wherein all parts and percentages are by weight:

As illustrated in the TABLES below, some of the sealing members are superior to others for use in the dynamic seal of a pressurized aerosol container. The TABLES below occasionally contain data that appear somewhat inconsistent with other data. These aberrant results are generally attributable to failure of several (e.g., one or two) vials in the test group.

In the TABLES that follow, "ID" represents the inside diameter of the diaphragm; "ss" indicates a stainless steel valve stem; "pl" indicates a Delrin™ acetal resin valve stem; "N" indicates the number of independent determinations used to evaluate the leak rate and valve delivery values. When two values are given, the first represents the number of determinations used to evaluate leak rate, the second represents the number of determinations used to evaluate valve delivery. Leak rate and valve delivery are shown along with standard deviation. Unless otherwise indicated the outside diameter of the diaphragms is 8.64 mm (0.34 inch) and the thickness is 0.89 mm (0.035 inch).

For comparative purposes, diaphragms were prepared from "Buna" rubber and from butyl rubber, both materials being commonly used in commercially available metered dose inhalers. These diaphragms were tested (upright storage of the aerosol canisters at a temperature of 30° C.) with formulations as indicated in TABLES 1 and 2 below.

| Formulation | Albuterol Sulfate (%) | Beclomethasone Dipropionate (%) | Oleic Acid (%) | Ethanol (%) | HFC 134a (%) | HFC 227 (%) |
|---|---|---|---|---|---|---|
| 1 | 0.385 | — | 0.03 | 15 | 84.585 | — |
| 2 | — | 0.084 | — | 7.993 | 91.923 | — |
| 3 | 0.5 | — | — | — | 99.5 | — |
| 4 | 0.5 | — | — | 10 | 89.5 | — |
| 5 | 0.5 | — | — | 10 | — | 89.5 |
| 6 | 0.5 | — | — | — | — | 99.5 |

TABLE 1

BUNA RUBBER

| Formulation | ID (mm) | Stem | Time (Weeks) | N | Leak Rate (mg/yr) | Valve Delivery (mg/actuation) |
|---|---|---|---|---|---|---|
| 4 | 2.11 | ss | 0 | 20/12 | — | 50.56 ± 1.70 |
| | | | 4 | | 386 ± 20 | 51.11 ± 1.33 |
| | | | 12 | | 377 ± 14 | 53.82 ± 1.77 |
| | 2.24 | ss | 0 | 20/12 | — | 52.81 ± 1.64 |
| | | | 4 | | 347 ± 49 | 52.97 ± 1.33 |
| | | | 12 | | 392 ± 13 | 54.19 ± 2.70 |

TABLE 1-continued

BUNA RUBBER

| Formulation | ID (mm) | Stem | Time (Weeks) | N | Leak Rate (mg/yr) | Valve Delivery (mg/actuation) |
|---|---|---|---|---|---|---|
| | 2.36 | ss | 0 | 20/12 | — | 53.05 ± 1.42 |
| | | | 4 | | 345 ± 12 | 51.88 ± 3.76 |
| | | | 12 | | 386 ± 13 | 54.14 ± 1.79 |
| | 2.49 | ss | 0 | 20/12 | — | 53.88 ± 1.80 |
| | | | 4 | | 345 ± 16 | 53.78 ± 1.02 |
| | | | 12 | | 388 ± 19 | 54.05 ± 1.14 |
| | 2.11 | pl | 0 | 20/12 | — | 50.62 ± 0.71 |
| | | | 4 | | 312 ± 18 | 49.00 ± 1.18 |
| | | | 12 | | 395 ± 160 | 51.02 ± 0.71 |
| | 2.24 | pl | 0 | 20/12 | — | 53.32 ± 1.80 |
| | | | 4 | | 335 ± 12 | 52.53 ± 2.37 |
| | | | 12 | | 380 ± 13 | 53.71 ± 0.79 |
| | 2.36 | pl | 0 | 20/12 | — | 51.22 ± 0.75 |
| | | | 4 | | 324 ± 19 | 49.94 ± 1.36 |
| | | | 12 | | 378 ± 22 | 51.00 ± 0.45 |
| | 2.49 | pl | 0 | 20/12 | — | 51.27 ± 0.60 |
| | | | 4 | | 322 ± 12 | 50.57 ± 0.62 |
| | | | 12 | | 368 ± 13 | 51.13 ± 0.63 |

TABLE 2

BUTYL RUBBER

| Formulation | ID (mm) | Stem | Time (Weeks) | N | Leak Rate (mg/yr) | Valve Delivery (mg/actuation) |
|---|---|---|---|---|---|---|
| 4 | 2.11 | ss | 0 | 20/12 | — | 58.86 ± 2.59 |
| | | | 4 | | 174 ± 24 | 57.98 ± 2.04 |
| | | | 12 | | 216 ± 16 | 58.13 ± 3.15 |
| | 2.24 | ss | 0 | 20/12 | — | 57.86 ± 2.49 |
| | | | 4 | | 152 ± 9 | 58.02 ± 1.27 |
| | | | 12 | | 197 ± 10 | 58.39 ± 3.32 |
| | 2.36 | ss | 0 | 20/12 | — | 59.12 ± 2.19 |
| | | | 4 | | 151 ± 8 | 58.72 ± 3.35 |
| | | | 12 | | 195 ± 9 | 58.92 ± 3.46 |
| | 2.49 | ss | 0 | 20/12 | — | 58.74 ± 2.54 |
| | | | 4 | | 168 ± 28 | 58.02 ± 2.14 |
| | | | 12 | | 208 ± 30 | 60.59 ± 4.11 |
| | 2.11 | pl | 0 | 20/12 | — | 55.92 ± 0.59 |
| | | | 4 | | 159 ± 12 | 54.45 ± 1.73 |
| | | | 12 | | 247 ± 160 | 54.62 ± 1.04 |
| | 2.24 | pl | 0 | 20/12 | — | 56.31 ± 0.28 |
| | | | 4 | | 169 ± 25 | 54.50 ± 3.10 |
| | | | 12 | | 218 ± 22 | 54.37 ± 2.59 |
| | 2.36 | pl | 0 | 20/12 | — | 56.20 ± 0.73 |
| | | | 4 | | 161 ± 14 | 54.32 ± 1.58 |
| | | | 12 | | 211 ± 15 | 55.04 ± 0.78 |
| | 2.49 | pl | 0 | 20/12 | — | 56.67 ± 1.11 |
| | | | 4 | | 156 ± 11 | 55.16 ± 0.43 |
| | | | 12 | | 204 ± 11 | 55.24 ± 0.78 |

The results in TABLES 1 and 2 show that, when used with the indicated formulations, "Buna" diaphragms generally exhibit leak rates higher than 300 mg/year with generally acceptable valve delivery variability. The results also show that the butyl rubber diaphragms exhibit acceptable leak rates when used with the indicated formulations but valve delivery variability is not acceptable.

Hand cut diaphragms were prepared from the materials set forth in TABLES 3–9 below. The diaphragms were incorporated into 50 microliter SPRAYMISER™ metered dose aerosol valves and tested (inverted storage of the aerosol canisters at 40° C., except in connection with TABLE 9, wherein storage temperature was 30° C.) with the formulations indicated in the respective TABLES. The absence of an entry indicates that no measurement was made.

TABLE 3

SANTOPRENE ™ RESIN 271-64

| Formulation | ID (mm) | Time (Weeks) | Leak Rate (mg/yr) ± SD |
|---|---|---|---|
| 3 | 2.29 | 1 | 44 ± 10 |
| | 2.29 | 3 | 87 ± 5 |
| | 2.29 | 6 | 87 ± 4 |
| | 2.41 | 1 | 37 ± 11 |
| | 2.41 | 3 | 86 ± 9 |
| | 2.41 | 6 | 86 ± 9 |

TABLE 3-continued

SANTOPRENE ™ RESIN 271-64

| Formulation | ID (mm) | Time (Weeks) | Leak Rate (mg/yr) ± SD |
|---|---|---|---|
| | 2.54 | 1 | 36 ± 7 |
| | 2.54 | 3 | 88 ± 6 |
| | 2.54 | 6 | 90 ± 5 |

TABLE 4

SANTOPRENE ™ RESIN 271-73

| Formulation | ID (mm) | Time (Weeks) | Leak Rate (mg/yr) ± SD |
|---|---|---|---|
| 3 | 2.29 | 1 | 31 ± 8 |
| | 2.29 | 3 | 90 ± 10 |
| | 2.29 | 6 | 88 ± 8 |
| | 2.41 | 1 | 45 ± 12 |
| | 2.41 | 3 | 99 ± 12 |
| | 2.41 | 6 | 90 ± 10 |
| | 2.54 | 1 | 44 ± 10 |
| | 2.54 | 3 | 92 ± 10 |
| | 2.54 | 6 | 90 ± 6 |

TABLE 5

SANTOPRENE ™ RESIN 271-80

| Formulation | ID (mm) | Time (Weeks) | Leak Rate (mg/yr) ± SD |
|---|---|---|---|
| 3 | 2.29 | 1 | 21 ± 7 |
| | 2.29 | 3 | 84 ± 10 |
| | 2.29 | 6 | 82 ± 8 |
| | 2.41 | 1 | 36 ± 15 |
| | 2.41 | 3 | 98 ± 15 |
| | 2.41 | 6 | 98 ± 12 |
| | 2.54 | 1 | 37 ± 8 |
| | 2.54 | 3 | 97 ± 10 |
| | 2.54 | 6 | 96 ± 9 |

TABLE 6

SANTOPRENE ™ RESIN 271-64

| Formulation | ID (mm) | Time (Weeks) | Leak Rate (mg/yr) ± SD |
|---|---|---|---|
| 4 | 2.29 | 1 | 255 ± 35 |
| | 2.29 | 3 | 360 ± 34 |
| | 2.29 | 6 | 320 ± 28 |
| | 2.41 | 1 | 252 ± 26 |
| | 2.41 | 3 | 374 ± 56 |
| | 2.41 | 6 | 335 ± 21 |
| | 2.54 | 1 | 260 ± 29 |
| | 2.54 | 3 | 380 ± 28 |
| | 2.54 | 6 | 351 ± 24 |

TABLE 7

SANTOPRENE ™ RESIN 271-73

| Formulation | ID (mm) | Time (Weeks) | Leak Rate (mg/yr) ± SD |
|---|---|---|---|
| 4 | 2.29 | 1 | 230 ± 24 |
| | 2.29 | 3 | 345 ± 24 |
| | 2.29 | 6 | 310 ± 20 |
| | 2.41 | 1 | 254 ± 31 |
| | 2.41 | 3 | 367 ± 28 |
| | 2.41 | 6 | 318 ± 22 |
| | 2.54 | 1 | 244 ± 28 |

TABLE 7-continued

SANTOPRENE ™ RESIN 271-73

| Formulation | ID (mm) | Time (Weeks) | Leak Rate (mg/yr) ± SD |
|---|---|---|---|
| | 2.54 | 3 | 356 ± 30 |
| | 2.54 | 6 | 326 ± 26 |

TABLE 8

SANTOPRENE ™ RESIN 271-80

| Formulation | ID (mm) | Time (Weeks) | Leak Rate (mg/yr) ± SD |
|---|---|---|---|
| 4 | 2.29 | 1 | 257 ± 35 |
| | 2.29 | 3 | 363 ± 36 |
| | 2.29 | 6 | 330 ± 31 |
| | 2.41 | 1 | 267 ± 36 |
| | 2.41 | 3 | 365 ± 35 |
| | 2.41 | 6 | 341 ± 39 |
| | 2.54 | 1 | 257 ± 25 |
| | 2.54 | 3 | 360 ± 24 |
| | 2.54 | 6 | 340 ± 19 |

TABLE 9

KIRKHILL KL70L3866 EPDM RUBBER

| Formulation | ID (mm) | Time (Weeks) | Leak Rate (mg/yr) |
|---|---|---|---|
| 1 | 2.49 | 1 | 146 |
| | 2.49 | 3 | 206 |
| | 2.49 | 6 | 248 |
| 2 | 2.49 | 1 | 87 |
| | 2.49 | 3 | 141 |
| | 2.49 | 6 | 174 |

The results in TABLES 3–9 above show that the indicated materials have acceptable leak rate and valve delivery variability when used as diaphragm materials in metered dose inhalers containing formulations with HFC-134a as the propellant.

Certain thermoplastic elastomer alloy materials were extruded into a sheet 1.0 mm (0.040 inch) thick. Diaphragms having an inside diameter of 2.4 mm (0.095 inch) and an outside diameter of 8.64 mm (0.340 inch) were punched and then soaked for 11 days at 20° C. in the indicated formulation, and measured for dimensional stability. Results are shown in TABLE 10 below.

TABLE 10

| Material | Formulation | ID (% Change) | OD (% Change) |
|---|---|---|---|
| SANTOPRENE 271-64 | 3 | −2.5 | 3.7 |
| | 4 | −1.1 | 0.3 |
| SANTOPRENE 271-73 | 3 | 0 | −0.4 |
| | 4 | −0.4 | −0.4 |
| SANTOPRENE 271-80 | 3 | 2.2 | −0.3 |
| | 4 | −0.9 | −1.4 |

Diaphragms were punched from a sheet of an EPDM rubber material 0.89 mm (0.035 inch) thick. ID was 2.49 mm (0.098 inch) and OD was 8.64 mm (0.340 inch). The diaphragms were soaked for eleven (11) days, at 30° C. in the indicated formulation. Dimensional stability was measured. Results are shown in TABLE 11 below.

TABLE 11

| Material | Formulation | ID (% Change) | OD (% Change) |
|---|---|---|---|
| KL70L3841 | 3 | −0.65 | 0.6 |
| KL70L3866 | 3 | −1.1 | 0.6 |
| KL70L3841 | 4 | −1.3 | 0.2 |
| KL70L3866 | 4 | −0.1 | 0.1 |

The exemplified materials show suitable dimensional stability in the indicated formulations.

A thermoplastic elastomer alloy material based on polypropylene and an EPDM rubber (SANTOPRENE™ 271-64) was extruded into a sheet 1.0 mm (0.040 inch) thick. Diaphragms were punched out having an ID of 2.4 mm (0.095 inch) and an OD of 8.64 mm (0.340 inch). The diaphragms were incorporated into 50 µL SPRAYMISER™ metered dose aerosol valves and tested (the aerosol canisters were stored at 30° C., upright for leak rate measurement and inverted for valve delivery and through-life valve delivery) with the formulations listed in TABLES 12 and 13 below.

TABLE 12

| Formulation | Time (weeks) | Valve Delivery (mg ± SD) | Leak Rate (mg/yr ± SD) |
|---|---|---|---|
| 5 | 0 | 63.9 ± 1.0 | — |
|   | 4 | 66.3 ± 0.98 | 22.2 ± 0.50 |
|   | 6 | 65.4 ± 0.91 | 29.4 ± 4.2 |
| 6 | 0 | 72.2 ± 1.0 | — |
|   | 4 | 72.2 ± 1.7 | 11.7 ± 3.4 |
|   | 6 | 72.0 ± 0.90 | 14.1 ± 1.1 |

TABLE 13

| | | Through-Life Valve Delivery (mg ± SD) | |
|---|---|---|---|
| Formulation | Time (weeks) | Vial 1 | Vial 2 |
| 5 | 0 | — | — |
|   | 4 | 65.3 ± 0.39 | 64.7 ± 0.40 |
|   | 6 | 66.8 ± 0.63 | 65.1 ± 0.58 |
| 6 | 0 | — | — |
|   | 4 | 40.3 ± 22.3 | 49.4 ± 14.4 |
|   | 6 | 48.4 ± 16.6 | 40.3 ± 20.1 |

The results in TABLE 12 show that the exemplified material has a very low leak rate when used with the indicated formulations. TABLE 13 shows suitable through-life valve delivery for Formulation 5. Formulation 6, however, having no ethanol present, is seen to exhibit high variability of valve delivery over the life of the formulation.

The claimed invention is:

1. A device for delivering an aerosol, comprising: a valve stem, a diaphragm comprising an ethylene-propylene-diene rubber free of silicone adhesive agents and having walls defining a diaphragm aperture, and a casing member having walls defining a formulation chamber and a casing aperture, wherein the valve stem passes through the diaphragm aperture and the casing aperture and is in slidable sealing engagement with the diaphragm aperture, and wherein the diaphragm is in sealing engagement with the casing member, the device having contained in the formulation chamber thereof a medicinal aerosol formulation wherein the medicinal aerosol formulation comprises 1,1,1,2-tetrafluoroethane or 1,1,1,2,3,3,3-heptafluoropropane.

2. A device according to claim 1 wherein the diaphragm is stable to dimensional change when exposed to the medicinal aerosol formulation.

3. A device according to claim 1, wherein the ethylene-propylene-diene rubber is the only polymer component of the diaphragm.

4. A device according to claim 1, wherein the ethylene-propylene-diene rubber is present in the form of particles dispersed in a continuous thermoplastic matrix.

5. A device according to claim 4, wherein the thermoplastic matrix comprises polypropylene or polyethylene.

6. A device according to claim 2, wherein the ethylene-propylene-diene rubber is the only polymer component of the diaphragm.

7. A device according to claim 2, wherein the ethylene-propylene-diene rubber is present in the form of particles dispersed in a continuous thermoplastic matrix.

8. A device according to claim 7, wherein the thermoplastic matrix comprises polypropylene or polyethylene.

* * * * *